(12) United States Patent
Shekhar

(10) Patent No.: US 11,872,240 B2
(45) Date of Patent: Jan. 16, 2024

(54) ANTIMICROBIAL FORMULATIONS COMPRISING VANCOMYCIN OR TOBRAMYCIN

(71) Applicants: Chander Shekhar, New Delhi (IN); Khalid Khan, New Delhi (IN); Shruti Kaushik, New Delhi (IN)

(72) Inventor: Chander Shekhar, New Delhi (IN)

(73) Assignees: Chander Shekhar, Delhi (IN); Khalid Khan, Delhi (IN); Shruti Kaushik, Delhi (IN)

(*) Notice: Subject to any disclaimer, the term of this patent is extended or adjusted under 35 U.S.C. 154(b) by 96 days.

(21) Appl. No.: 17/266,667

(22) PCT Filed: Aug. 6, 2019

(86) PCT No.: PCT/IB2019/056683
§ 371 (c)(1),
(2) Date: Feb. 8, 2021

(87) PCT Pub. No.: WO2020/031083
PCT Pub. Date: Feb. 13, 2020

(65) Prior Publication Data
US 2021/0308164 A1    Oct. 7, 2021

(30) Foreign Application Priority Data
Aug. 6, 2018 (IN) .............. 201811029497

(51) Int. Cl.
*A61K 31/7036* (2006.01)
*A61K 31/702* (2006.01)
*A61K 47/10* (2017.01)

(52) U.S. Cl.
CPC ........ *A61K 31/7036* (2013.01); *A61K 31/702* (2013.01); *A61K 47/10* (2013.01)

(58) Field of Classification Search
None
See application file for complete search history.

(56) References Cited

U.S. PATENT DOCUMENTS

| | | | | |
|---|---|---|---|---|
| 4,650,790 A | * | 3/1987 | Simon | A61K 31/215 514/35 |
| 8,785,421 B1 | * | 7/2014 | Lippolis | A61K 45/06 514/165 |
| 2004/0151765 A1 | | 8/2004 | Ritchie et al. | |
| 2005/0153876 A1 | * | 7/2005 | Cameron | A61P 31/04 514/2.7 |
| 2006/0194008 A1 | * | 8/2006 | Schwartz | C23C 14/06 428/34.4 |
| 2007/0105758 A1 | | 5/2007 | May et al. | |
| 2007/0244059 A1 | * | 10/2007 | Karaolis | A61P 31/02 514/44 R |
| 2008/0057129 A1 | | 3/2008 | Lerner et al. | |
| 2010/0273748 A1 | * | 10/2010 | Gallo | A61P 17/02 435/375 |
| 2011/0275587 A1 | | 11/2011 | Reitz et al. | |
| 2018/0036226 A1 | * | 2/2018 | Rutolo, Jr. | A61K 33/42 |

\* cited by examiner

*Primary Examiner* — Dale R Miller

(57) ABSTRACT

The present invention relates to antimicrobial formulations comprising Vitamin D as carrier loaded with an antibiotic. More specifically, the present invention relates to antimicrobial compositions comprising vitamin D as carrier loaded with an antibiotic for controlling infections and managing potentially infected wounds or infected wounds or treating infected implants used in orthopaedic surgery and various other conditions leading to healing of the wounds and avoidance of development of antibacterial resistance and avoiding complications related to the use of prolonged antibiotics by systemic route.

7 Claims, No Drawings

ANTIMICROBIAL FORMULATIONS COMPRISING VANCOMYCIN OR TOBRAMYCIN

FIELD OF THE INVENTION

The present invention relates to antimicrobial formulations comprising Vitamin D as carrier loaded with an antibiotic. More specifically, the present invention relates to antimicrobial compositions comprising vitamin D as carrier loaded with an antibiotic for controlling infections and managing potentially infected wounds or infected wounds or treating infected implants used in orthopaedic surgery and various other conditions leading to healing of the wounds and avoidance of development of antibacterial resistance and avoiding complications related to the use of prolonged antibiotics by systemic route.

BACKGROUND OF THE INVENTION

All types of open infected wounds of the musculoskeletal system are the most prevalent types of infections in injuries and other situations are the leading causes of significant morbidity in all age groups. The standard prophylactic treatment commonly used is systemic antibiotic therapy. However, systemic distribution is reduced in some complex musculoskeletal wounds due to compromised vasculature thus allowing for proliferation of contaminating bacteria leading to infection, thus severely impairs wound healing and can get complicated even when antibiotic resistant and/or biofilm-forming bacterial strains are present resulting in the need for higher concentration of systemic antibiotics causing additional pain and disability to the patient as well as very great economic cost to society in the form of direct medical cost, lost earnings, and disability payments. Further, merely increasing the dosage of systemic antibiotics can help clear infection, but may lead to adverse side effects. The most commonly strains of bacteria responsible for causing wound infections mainly include are *S. aureus, S. epidermidis*, coagulase-negative staphylococci, and *Pseudomonas aeruginosa*. It has further been reported that the patients still develop infections even with systemic antibiotics delivered in a clinical setting. For instance, antibiotics present at levels below the minimum inhibitory concentration (MIC) in a *S. aureus* infection can lead to the development of more resistance to the antibiotic.

One could rationally associate the peaks and troughs of antibiotic bioavailability seen in systemic delivery with the development of antibiotic resistant bacterial strains and bio-film.

To further overcome the disadvantages of the systemic antibiotic therapy, a local antibiotic delivery system could increase antibiotic levels at the musculoskeletal wound without increasing risk to the patient.

The most commonly used antibiotics for local delivery to musculoskeletal trauma includes vancomycin and tobramycin. Both antibiotics are considered reliable because they are capable of sustained activity over an extended elution time, storage time, or variable environmental conditions such as a low pH. Vancomycin is effective against severe infections caused due to susceptible methicillin-resistant (beta-lactam resistant) staphylococci in penicillin-allergic patients; patients who cannot receive or have failed to respond to other drugs, including penicillins and cephalosporins; and for infections due to vancomycin-susceptible organisms resistant to other antimicrobials while tobramycin or gentamycin or amikacin has a broad spectrum of efficacy including against Gram negative bacteria, such as the bio-film forming *P. aeruginosa*.

Further, the commonly used carrier material in local antibiotic delivery systems includes polymethylmethacrylate, bone cement, POP pellets, collagen sponge, fibrin sealant, Hydrosy apatite blocks, Poly-glycolide implants, di Lactate polymer and calcium sulfate, which increases the local antibiotic levels within the tissue surrounding a wound; which could enhance treatment outcome for contaminated wounds. However, the current options present limitations such as surgical removal after a period of time, rapid degradation, or a limited choice of antibiotics utilized at the time of application. Further polymethylmethacrylate (PMMA) provides number of significant disadvantages such as it is dense, acrylic, and non-resorbing material, which generally must be removed in a second surgical procedure when its function has been fulfilled to avoid becoming a nidus for future infection. Also, it can release sub-inhibitory concentrations of drugs over an extended implantation period, and bacteria adherent to PMMA cement thus can acquire resistance to the loaded antibiotic because of long exposure to the sub-inhibitory concentrations. Also, PMMA is not suitable for delivery of thermo-sensitive antibiotics because of the high temperatures generated during PMMA curing.

Development of anti-biotic resistance with prolonged use of antibiotic is well known and the emergence of resistant bacteria is difficult to control and the bio-films which form around the infected sites in infected implants are difficult to eradicate. Therefore, the present limitations provide the need for the development of a novel and cost effective local drug delivery system with suitable bio-carrier in order to provide enhanced treatment over current approaches, particularly in complex trauma wounds or patients with infection risk factors i.e., diabetes, positive skin cultures, history of infection.

OBJECT OF THE INVENTION

The main object of the present invention is to provide an antimicrobial composition comprising Vitamin D as carrier for local delivery of antibiotics for controlling infections and managing potentially infected wounds or infected wounds or treating infected implants used in orthopedic surgery and various other such indications.

Another object of the present invention is to provide a method of preparing an antimicrobial formulation comprising Vitamin D for local delivery of the drugs preferably, antibiotics is not limited to aminoglycosides, Beta-lactam agents, and Quinolones.

Yet another object of the present invention is to provide an antimicrobial composition comprising Vitamin D as carrier which is very safe, cost-effective, and extremely effective without any complications in controlling and completely eradicating infections.

SUMMARY OF THE INVENTION

The present invention relates to antimicrobial formulations comprising vitamin D as carrier of local delivery of the drugs preferably, antibiotics. More specifically, the present invention relates to vitamin D as carrier beads for local delivery of the antibiotic drugs/components for controlling infections and managing potentially infected wounds or infected wounds or treating infected implants used in orthopedic surgery and various other such indications.

In an embodiment the present invention provides a pharmaceutical composition comprising of an antimicrobial agent or a pharmaceutically acceptable salt or a combination of one or more antimicrobial agents or a pharmaceutically acceptable salt; a pharmaceutically acceptable carrier; wherein, the antimicrobial agent includes but is not limited to vancomycin, tobramycin; and the pharmaceutically acceptable carrier includes but is not limited to Vitamin $D_3$.

In another embodiment the present invention relates to a method of preparing antimicrobial formulation comprising Vitamin D as carrier for local delivery of the drugs, preferably antibiotic comprising steps of: (a) mixing Vitamin D with antibiotic to obtain a mixture in a desired ratio; (b) blending the mixture obtained in step (a) thoroughly to obtain a homogenous mixture; (c) mixing the mixture obtained in step (b) with sterile water to obtain a smooth paste; (d) filling and pressing the smooth paste obtained in step (c) into the cavities of the flexible mold to obtain beads; (e) leaving the beads obtained in step (d) undisturbed and letting it dehydrate until hard; and (f) removing the beads from the flexible mold to obtain Vitamin D carrier beads.

In yet another embodiment the present invention, relates to using Vitamin D as carrier for local delivery of the drugs, preferably antibiotic which is very safe, cost-effective, and extremely effective without any complications in controlling and completely eradicating infections.

In yet another embodiment the present invention, relates to using Vitamin D as carrier for local delivery of the drugs, preferably antibiotics which is not limited to aminoglycosides, Beta-lactam agents, Quinolones.

In yet another embodiment the present invention, relates to using Vitamin D as carrier of local delivery of the drugs, preferably antibiotics for controlling infections and managing potentially infected wounds or infected wounds or treating infected implants used in orthopedic surgery and various other conditions.

DETAILED DESCRIPTION OF THE INVENTION

The present invention will now be described more fully hereinafter. This invention may, however, be embodied in many different forms and should not be construed as being limited to the embodiment set forth herein. Rather, the embodiment is provided so that this disclosure will be thorough, and will fully convey the scope of the invention to those skilled in the art.

The present invention relates to an antimicrobial formulation comprising Vitamin D as preferred carrier for local delivery of the drugs preferably, antibiotics. More specifically, the present invention relates to vitamin D as carrier for local delivery of the drugs, preferably antibiotics for controlling infections managing potentially infected wounds or infected wounds or treating infected implants used in orthopedic surgery and various other conditions.

In the main embodiment the present invention provides a pharmaceutical composition comprising of an antimicrobial agent or a pharmaceutically acceptable salt or a combination of one or more antimicrobial agents or a pharmaceutically acceptable salt; a pharmaceutically acceptable carrier; wherein, the antimicrobial agent includes but is not limited to vancomycin, tobramycin; and the pharmaceutically acceptable carrier includes but is not limited to Vitamin $D_3$. The composition optionally includes but is not limited to buffering agents, preservatives, coloring agents, and stabilizers.

In yet another embodiment the present invention relates to a pharmaceutically acceptable carrier which includes but is not limited to Vitamin $D_3$. Vitamin $D_3$ is actually a fat-soluble prohormone steroid that has endocrine, paracrine, and autocrine functions. The endocrine effects of vitamin $D_3$ are mainly involved in serum calcium homeostasis. The paracrine and autocrine effects of vitamin $D_3$ depend on genetic transcription, unique to the type of cell expressing nuclear vitamin D receptors. Vitamin $D_3$ loosely binds to the antibiotic which includes but is not limited to tobramycin and get transported to the deeper parts of the skin and connective tissues where it gets released for antimicrobial activity; immunomodulator activity of vitamin is additive to produce fast healing effects in complicated wounds. It also has an important role in modulating the innate and adaptive immune system, which influences the production of important endogenous antimicrobial peptides such as cathelicidin and regulating the inflammatory cascade. Cathelicidin is an antimicrobial peptide that is able to directly kill pathogens or bind to the endotoxins. It is active against viruses and other bacteria like *Mycobacterium tuberculosis*. Vitamin $D_3$ also regulates the adaptive immune system particularly T-cells (TH1 cells, TH2 cells, TH17 cells, and T regulatory cells). Finally, vitamin D3 also regulates the inflammatory cascade by modulating the nuclear factor κB pathway.

In yet another preferred embodiment, the present invention relates to a method of preparing an antimicrobial formulation comprising Vitamin D as carrier for local delivery of the drugs, preferably antibiotics comprising steps of: (a) mixing Vitamin D (calcirol) with antibiotic powder to obtain a mixture in a desired ratio; (b) blending the mixture obtained in step (a) thoroughly to obtain a homogenous mixture; (c) mixing the mixture obtained in step (b) with sterile water to obtain a smooth paste; (d) filling and pressing the smooth paste obtained in step (c) into the cavities of the flexible mold to obtain beads; (e) leaving the beads obtained in step (d) undisturbed and letting it dehydrate until hard; and (f) removing the beads from the flexible mold to obtain Vitamin D carrier beads.

In yet another preferred embodiment, the present invention relates to using Vitamin D as carrier for local delivery of the drugs preferably, antibiotics which is stable, water soluble, active against the most common bacterial pathogens involved in bone and soft tissue infections, is released locally at concentration exceeding several times, usually ten times, have low rate of allergic reaction, low rate of primary resistance, not produce supra infections, is very safe, cost-effective, and extremely effective without any complications in controlling and completely eradicating infections.

In yet another preferred embodiment, the present invention relates to using Vitamin D as carrier for local delivery of the drugs preferably, antibiotics for controlling infections managing potentially infected wounds or infected wounds or treating infected implants used in orthopedic surgery and various other conditions.

In yet another preferred embodiment, the present invention relates to providing Vitamin D as carrier for local delivery of the drugs preferably, antibiotics not limited to Amino glycosides Beta lactam agents, Quinolones and the amino glycosides not limited to tobramycin, gentamycin or vancomycin. Table 1 compares Vitamin $D_3$ Granules versus Currently Used Delivery Carriers in Local Antibiotic Delivery System. Though several biodegradable delivery systems have been developed, such as calcium sulfate, collagen sponges, calcium phosphate, and polylactic acid, each of these methods have specific disadvantages as shown in Table 1. Degradable collagen fleeces and calcium-based carriers are known to release large amount of antibiotics in the first 24 hours after implantation. While prolonged release is not guaranteed, they absorb large amount of water, stimulate seromas, and increase the risk of secondary infection. Polyglycolic acid carriers are known to produce acidic degradation products, which can lead to resorption of the bone. Considering the bacteriological finding in bone and soft tissue infections that is chronic osteomyelitis caused by *Staphylococcus aureus*, Enterobacteriaceae, and *Pseudomonas aeruginosa*, the most acceptable agent in local delivery systems are aminoglycosides and to a lesser extent various β-lactam agents and quinolones.

formulation to work in the biological system, are called as excipients. Excipients have a broad range of functionalities in making formulations in the form of bulking agents, binders, disintegrants, flavors, glidants, lubricants, preservatives, permeation enhancers, solubility enhancers, preservatives and sweeteners, etc. Further to enhance the drug bioavailability, excipients are used which enhance the stability and increases the solubility of the drug. Solubility enhancing excipients are mainly categorized into three sections called as a polymer, surfactant, and lipid based. However, polymer based excipients are widely used for solubility enrichment process. The surfactants in surfactant based

TABLE 1

Vitamin $D_3$ Granules versus Currently Used Delivery Carriers in Local Antibiotic Delivery System

| Carrier | Antibiotic | Biodegradable | Promote Tissue Growth | Fat Soluble | Increase Bone Mineral Density | Side Effects |
|---|---|---|---|---|---|---|
| PMMA beads[12] | Gentamycin, tobramycin, vancomycin | x | x | x | x | Secondary infection |
| Calcium sulfate | Tobramycin | ✓ | x | x | — | Emergence of resistant bacteria |
| Collagen sponges | Gentamycin, tobramycin, vancomycin | ✓ | x | x | x | Can contain impurities |
| Polylactic acid | Gentamycin, tobramycin, vancomycin | ✓ | x | x | x | Local tissue reaction |
| Vitamin $D_3$ granules | Gentamycin, tobramycin, vancomycin | ✓ | ✓ | ✓ | ✓ | None |

In yet another preferred embodiment of the present invention, the antimicrobial composition comprising 1 gm Vitamin $D_3$ carrier and 5-20 mg of an antibiotic drug, or alternately can have higher possible carrier to drug ratio in range of 100:1 to 1:1, or depending on the drug composition, the ratio can vary to modulate bioavailability and least cytotoxicity.

In yet another preferred embodiment of the present invention, the antimicrobial formulation is formulated for delayed/controlled drug delivery, wherein, the delivery is delayed in the range of 1 to 15 days.

In yet another preferred embodiment, the present invention relates to using Vitamin D as carrier for local delivery of drugs preferably, antibiotics through various modes of drug carrier delivery systems not limited to Polymer based nanoparticles, liposomes or phospholipid vesicles and other colloidal systems which involves micro or nano encapsulation of Vitamin D along with the drug. Depending on the hydrophobic nature of Vitamin D, a hydrophobic polymer matrix is crucial to the drug loading and the most PLGA is identified as primary choice which has competence to encapsulate drugs of poor solubility.

In yet another preferred embodiment, the present invention relates to antimicrobial formulation comprising Vitamin D as carrier wherein the mode of administration of the composition is not limited to enteral route, parenteral route, topical route or arterial route. The enteral route mainly comprises of oral, sublingual and rectal while the parenteral route comprises of intravenous, intramuscular, subcutaneous and inhalation. Further, the topical route comprises skin, mucous membrane, mouth and pharynx, eyes, ears, nose and gastrointestinal tract while in the arterial route the drug is injected into the artery that is supplying the blood to the desired site so that localized action is achieved.

In yet another preferred embodiment, the present invention relates to antimicrobial formulation comprising Vitamin D granules as carrier and excipients. Pharmaceutical drug delivery systems consist of additional therapeutically inactive constituents other than APIs which are required for the excipient can facilitate their solubilization. Further, surfactants can solubilize the poorly soluble drug molecules by micelle formation or by acting as co-solvents. The combination of lipophilic surfactants, hydrophilic surfactants, water-soluble co-solvents, triglyceride oils, co-surfactants can build the efficient and stable self-emulsifying drug delivery system which can improve drug solubility and oral absorption.

In yet another preferred embodiment, the Vitamin D carrier for local delivery of drugs preferably, antibiotics is formulated in any dosage form suitable for topical administration preferably, the composition is in a form such as a cream, ointment, gel, lotion, foam, powder, aerosol, spray, or liquid solution or may be in form of a polymeric patch containing drug preferably, anti-biotic which facilitates transdermal delivery for treating the infection which aids in managing the release of drug for longer period of time in a sustained manner. The topical administration is given for open wounds not limited to incisions or incised wounds, lacerations, abrasions, avulsions, puncture wounds, penetration wounds and gunshot wounds. Further, the topical administration can also be used in cases of burns.

The local delivery of the antibiotics using Vitamin D as carrier is applicable in compound injuries of the limbs sustained in road traffic accidents, non-healing infected wounds, post-operative patients in orthopedics with infected implants with open discharging wounds which are not healing, in surgical situations where there occurs formation of dead spaces in deep layers or superficial layers of the wounds with possibility of formation of infected hematoma, in degloving wounds, in surgeries where the flaps whether vascularised flaps or rotation flaps or facio-cutaneous flaps are required to cover the defects of the soft tissues and the bone, in situations where plates & screws are being used especially when the injuries are compound in nature. Further, at various sites in general surgical conditions where the patient immunity is low, where the patient is severely diabetic and on several medications like disease-modifying anti-rheumatic drugs (DMRD) in rheumatoid arthritis or immune-suppressive drugs in other conditions and other miscellaneous conditions where the treating surgeon decides according to his personal experiences.

In yet another preferred embodiment of the present invention, the composition comprises effective amount of mixture of at least two antibiotic compounds such as vancomycin and tobramycin loaded on Vitamin D granules. The composition when applied directly onto the affected area, with or without repeating the dosage, shows quick recovery and antibiotic efficacy in shorter period of time.

In yet another preferred embodiment of the present invention, the composition comprises effective amount of mixture of at least two antibiotic compounds such as vancomycin and tobramycin loaded on Vitamin D granules. The ratio of antibiotics to Vitamin D may vary depending upon the type, location and severity of infection in the wounds. The amount of antibiotic dosage with respect to the amount of Vitamin D is increased in case of chronic wounds. However, in case of acute severity of the infection the amount of antibiotic dosage with respect to the amount of Vitamin D is reduced. Therefore, the amounts of antibiotics used in the composition as compared to the amounts of Vitamin D used in wound dressings may vary and is altered according to the severity of infection and type of wound encountered.

In an alternate embodiment, the present invention provides a composition comprising effective amount of vancomycin loaded on Vitamin D granules. The ratio of vancomycin with respect to the Vitamin D used in wound dressings may vary and is altered according to the severity of infection and type of wound encountered.

In another alternate embodiment, the present invention provides a composition comprising effective amount of tobramycin loaded on Vitamin D granules. The ratio of vancomycin with respect to the Vitamin D used in wound dressings may vary and is altered according to the severity of infection and type of wound encountered.

In an exemplary procedure for treating an infectious wound of size 3×3.5 sq. inch, 1 gm Vitamin $D_3$ granules i.e. equivalent to 60,000 IU were mixed with 60 mg Tobramycin. The mixture was applied to the wound resulting is complete healing within 4-5 days.

In another exemplary procedure for treating an infectious wound with pus, 1 gm Vitamin $D_3$ granules i.e. equivalent to 60,000 IU were mixed with 60 mg Tobramycin and 10-20 mg Vancomycin. The mixture was applied to the wound resulting is complete healing within 3-4 days.

In another exemplary procedure for treating an infectious wound of substantial size having moderate pus, 1 gm Vitamin $D_3$ granules i.e. equivalent to 60,000 IU were mixed with 60 mg Tobramycin and 5-10 mg Vancomycin. The mixture was applied to the wound resulting is complete healing within 4-5 days.

In another exemplary procedure for treating an infectious wound of substantial size having moderate pus, 1 gm Vitamin $D_3$ granules i.e. equivalent to 60,000 IU were mixed with 5-10 mg Vancomycin. The mixture was applied to the wound resulting is complete healing within 4-5 days.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A pharmaceutical composition comprising:
   an antimicrobial agent or a pharmaceutically acceptable salt thereof or a combination of antimicrobial agents or a pharmaceutically acceptable salts thereof;
   a pharmaceutically acceptable carrier; and
   at least one excipient;
   wherein,
   said antimicrobial agent is vancomycin in the range of 5-20 mg or tobramycin in the range of 55-65 mg;
   said combination of antimicrobial agents is a mixture of tobramycin, in the range of 55-65 mg, and vancomycin, in the range of 5-20 mg; and
   the pharmaceutically acceptable carrier is Vitamin $D_3$ in the range of 1-5 gm;
   the Vitamin $D_3$ is loaded with the antimicrobial agent; and
   the composition is applied topically for managing the infected open wounds within a time span of 7 days.

2. The composition as claimed in claim 1 wherein, the pharmaceutically acceptable carrier vitamin $D_3$ delivers antibiotic to an infected wound for eradicating infection, helping tissue healing and growth, promoting bone mineral density and avoiding the emergence of resistant bacteria.

3. The composition as claimed in claim 1 wherein, the at least one excipient comprises buffering agents, preservatives, coloring agents, tonicity agents, chelating agents, amino acids, stabilisers or other pharmaceutical excipients.

4. The composition as claimed in claim 1 wherein, the excipient is tryptophan.

5. The composition as claimed in claim 1, wherein the antimicrobial agent or a pharmaceutically acceptable salt or a combination of one or more antimicrobial agents or a pharmaceutically acceptable salt and the pharmaceutically acceptable carrier having ratio in range of 1:100 to 1:1 by weight.

6. The composition as claimed in claim 1, wherein the composition is formulated in forms selected from the group consisting of cream, ointment, gel, lotion, foam, powder, aerosol, spray, or liquid solution and a polymeric patch.

7. The composition as claimed in claim 1, wherein the composition is formulated for delayed/controlled drug delivery having delay in the range of 1 to 15 days.

* * * * *